United States Patent
Alexenko et al.

(10) Patent No.: US 6,829,941 B2
(45) Date of Patent: Dec. 14, 2004

(54) TUNNEL EFFECT NANODETECTOR OF MECHANICAL VIBRATIONS AND METHOD FOR PREPARATION THEREOF

(76) Inventors: Andrey Gennadievich Alexenko, 2 Serafimovicha St., Apt. 212, Moscow 109072 (RU); Mikhail Arsenovich Ananyan, 52 Leninsky Prospect, Apt. 430, Moscow 117333 (RU); Valery Leonidovich Dshkhunyan, 2 Pl. Yunosti, Apt. 19, Zelenograd, Moscow 103460 (RU); Vyacheslav Fedorovich Kolomeitzev, 3/5 Sirenevy Bulivar, Apt. 60, Moscow 105122 (RU); Petr Nikolaevich Luskinovich, 40 Altufievskoe Shosse, Apt. 357, Moscow 127577 (RU); Alexandr Borisovich Nevsky, 450 Zelenograd, Apt. 33, Moscow 103498 (RU); Oleg Alekseevich Orlov, 1228 Breckenridge Circle, Riva, MD (US) 21140

( * ) Notice: Subject to any disclaimer, the term of this patent is extended or adjusted under 35 U.S.C. 154(b) by 0 days.

(21) Appl. No.: 10/267,751

(22) Filed: Oct. 10, 2002

(65) Prior Publication Data

US 2004/0069063 A1 Apr. 15, 2004

(51) Int. Cl.$^7$ .............................................. G01H 11/06
(52) U.S. Cl. ........................ 73/658; 73/104; 250/338.1; 438/52
(58) Field of Search ................... 73/579, 658, 104–105; 250/338.1; 438/52

(56) References Cited

U.S. PATENT DOCUMENTS

| | | | |
|---|---|---|---|
| 5,290,102 A | * 3/1994 | Kaiser et al. ............... 374/120 |
| 5,315,247 A | 5/1994 | Kaiser et al. |
| 5,329,513 A | * 7/1994 | Nose et al. ................... 369/126 |
| 5,436,452 A | * 7/1995 | Kenny et al. ............. 250/338.1 |
| 5,438,196 A | * 8/1995 | Kitamura ..................... 250/306 |
| 5,449,909 A | 9/1995 | Kaiser et al. |
| 5,563,344 A | 10/1996 | Kaiser et al. ............. 73/514.24 |
| 5,576,250 A | 11/1996 | Diem et al. ................... 437/228 |
| RE37,203 E | * 6/2001 | Elings et al. ............... 250/306 |
| 6,268,604 B1 | * 7/2001 | Boyadzhyan-Sevak ... 250/338.1 |

FOREIGN PATENT DOCUMENTS

| | | | | |
|---|---|---|---|---|
| FR | 2 700 065 | | 7/1994 | |
| JP | 04034319 | * | 2/1992 | ........... G01H/11/06 |
| RU | 1449843 A | * | 1/1989 | ........... G01B/17/00 |
| RU | 94044849 | | 4/1996 | |
| RU | 2152044 | | 6/2000 | |
| WO | 95/10772 | | 4/1995 | |

* cited by examiner

Primary Examiner—Hezron Williams
Assistant Examiner—Rose M. Miller
(74) Attorney, Agent, or Firm—Venable LLP; Eric J. Franklin

(57) ABSTRACT

A tunnel effect nanodetector. A gold plated sensor pin is single crystal silicon. A gold plated sensor membrane is polycrystalline silicon over a pin. Through holes are in the membrane and gold. Corrugations are along membrane boundaries. The nanodetector includes a unit for maintenance of gap between the pin and membrane. The unit includes a deflection electrode and tunnel current limiter. Gold on the membrane is connected to an input voltage. Gold on the pin is connected to a tunnel current amplifier and tunnel current limiter, the output of which is connected to the deflection electrode. The capacitance measuring unit is connected to the deflection electrode and gold on the membrane. The tunnel current amplifier and capacitance measuring unit are connected to an A/D converter. The sensor, gap maintenance unit, tunnel current amplifier, capacitance measuring unit and A/D converter are a monolithic integrated circuit. The nanodetector electronics are polycrystalline silicon.

21 Claims, 2 Drawing Sheets

TUNNEL EFFECT NANODETECTOR OF MECHANICAL VIBRATIONS AND METHOD FOR PREPARATION THEREOF

FIELD OF THE INVENTION

The present invention relates basically to the control instrumentation and can be used for measuring physical-mechanical parameters of the environment and for nondestructive control of objects under diagnostics.

BACKGROUND OF THE INVENTION

A tunnel nanodetector of mechanical vibrations is known, which comprises a sensor made in a shape of a flexible cantilever and secured at one edge, a tip probe, from which the electron tunneling occurs, a perforated counter-electrode designed for electrostatic control of the sensor and a fixed electrode. The electrodes enabling the occurrence of tunneling the electrons between them are plated with a noble metal, for example, gold. The action principle of the tunnel nanodetector is based on measuring the tunnel current running through the gap between an electrode of the sensor and the fixed electrode. The current value depends on the size of the gap. (W. C. Young, Roark's Formulas for Stress and Strain, New York: Mc Graw-Hill, 1989).

A disadvantage of the known tunnel nanodetector of mechanical vibrations is an insufficient vibration-and shock strength and a high level of inherent noise, this doesn't allow to carry out a reliable measuring of physical-mechanical characteristics of objects to be sensed.

A tunnel nanodetector of mechanical vibrations is known, which comprises a sensor made in a shape of a tip probe plated with a layer of a noble metal, over which at the level of from parts of nanometer to parts of micron a corrugated membrane is located being plated with a layer of a noble metal from the tip side, said layer of the noble metal is connected to the input voltage source. Additionally said tunnel nanodetector comprises a unit intended to control the gap value between the tip and membrane containing a deflection electrode made of a layer of the noble metal deposited around the tip, a tunnel current amplifier placed between the layer of the noble metal deposited on the tip and the first input of the A/D converter (Kenny T. W. et al. Wide-Bandwidth Electromechanical Actuators for Tunneling Displacement Transducers. Journal of Micromechanical Systems, vol.3, No 3, 1994, p.99).

In accordance with the task to be solved and the common character of structural features the above described tunnel nanodetector of mechanical vibrations is mostly close to the invention and has been chosen as a prototype.

However, the known tunnel nanodetector of mechanical vibrations doesn't assure the needed super high sensitivity and magnification stability in the wide range of acoustical vibration energies what hinders to listen as the inherent noises of objects under diagnostics as the noises induced by background effects, therewith the system is adapted neither to the level nor to the spectrum of the input acoustic signal.

It is known a method for preparation of tunnel nanodetectors of mechanical vibrations based on using the planar semiconductor technology, which foresees the preparation and forming of plating layers for the tip and membrane of sensor, the forming of an insulation layer and forming of a plating layer for the deflection electrode.

In accordance with the known method the tip and membrane of the sensor are prepared at two separated silicon substrates, but the unit for control the gap value between the probe and membrane, the tunnel current amplifier and the A/D converter are prepared at an individual ceramic substrate (Kenny T. W. et al. Wide-Bandwidth Electromechanical Actuators for Tunneling Displacement Transducers. Journal of Micromechanical Systems, vol.3, No 3, 1994, p.99).

In accordance with the task to be solved and the common character of structural features the known method of fabricating the tunnel nanodetector of mechanical vibrations is mostly close to the invention and has been chosen as a prototype.

However the known method doesn't provide the required high accuracy and reproducibility of constructive-functional parameters of tunnel nanodetectors and is of a low economic efficiency.

SUMMARY OF THE INVENTION

A technical result of the invention is the development of a tunnel effect nanodetector of mechanical vibrations meeting the need to rise the sensitivity and to decrease the level of inherent noises when measuring the physical-mechanical parameters of objects under diagnostics, to increase the dynamic range by an order of magnitude during ultrasound examination of patients and to reduce the radiation level up to the safe dose, to provide the adaptation of the diagnostics system to be created on its basis to the level and to the spectrum of the input acoustical signal or to the value of acceleration coming from the diagnosed object as well as to provide the capability of revealing the micro structural faults in objects under diagnostics (in the field of power engineering, mechanical engineering, building).

The method for preparation of said tunnel effect nanodetector in conformity with the invention allows to assure a high sensitivity and reproducibility of their constructive-functional parameters and to provide high economic characteristics.

The essence of the invention consists in that the tunnel effect nanodetector of mechanical vibrations relates to the micro systems because several functional units with minimum sizes of all involved components are combined in a single body. Into that tunnel effect nanodetector comprising a sensitive element (sensor), consisting of a probe made in the form of a pin plated with the layer of a noble metal over which a corrugated membrane is placed with a gap, the size of which can change from parts of a nanometer to parts of a micron, the membrane from the side of the pin is plated with the layer of a noble metal connected to the source of input voltage, a gap control unit placed between the pin and membrane and containing a deflection electrode made of the layer of the noble metal deposited around the pin, a tunnel current amplifier located between the layer of the noble metal deposited on the pin and the first input of the A/D converter there is inserted a capacitance measuring unit, the inputs of which are connected to the deflection electrode and to the layer of the noble metal deposited on the membrane and the output is connected to the second input of the A/D converter. A unit for limiting the tunnel current value with its input connected to the layer of the noble metal deposited on the pin and with its output connected to the deflection electrode is put into the unit for control the gap between the pin and membrane. The through holes are made across the whole surface of the membrane and in the layer of the noble metal covering it.

The sensor, the gap control unit, the tunnel current amplifier, the capacitance measuring unit and the A/D converter are made in the form of monolithic integrated circuit, therewith the pin of the sensor is prepared from the single crystal silicon within the substrate body and the sensor membrane and the components of the gap control unit, tunnel current amplifier, capacitance measuring unit and A/D converter are made from the polycrystalline silicon.

The essence of the invention consists also in that the method for preparation of the tunnel effect nanodetector of mechanical vibrations being based on using the planar semiconductor technology and incorporating such steps as preparation of sensor's pin and membrane, forming the plating layers of the latter, forming the insulation layer and forming the plating layer for the deflection electrode should be realized as follows:

The sensor's pin and the recesses for membrane corrugations are formed within a monolith of silicon substrate, for this to achieve the mask layer of the silicon nitride is deposited from the gaseous phase, the photolithography is carried out followed by dry etching with forming the patterns of the pin and of recesses for membrane corrugations, the sections of silicon nitride mask layer to be removed are exposed to the reactive ion etching; the isotropic plasma-chemical etching, anisotropic reactive ion etching and local thermal oxidation are successively performed, thereafter the silicon nitride mask and also the layer of the silicon oxide are chemically stripped.

The insulation layer and the plating layers for the pin and the deflection electrode are formed, for this aim the silicon substrate is thermally oxidized and the silicon nitride layer is deposited from the gaseous phase, the vacuum deposition of the noble metal is performed, the photolithography is carried out followed by dry etching with forming the plating patterns of the pin and deflection electrode, the layer of the noble metal is exposed to the reactive ion etching, thereafter the mask layer is removed from the photoresist by plasma-chemical way.

The gap-forming layer is prepared, for this aim the layer of fusible phosphorous borosilicate glass is deposited from gaseous phase and fire-polished, the photolithography is carried out with obtaining the pattern of the gap-forming layer, the layer of the fusible phosphorous borosilicate glass is exposed to reactive ion etching, after that the high-melting layer of the silicon oxide is deposited from the gaseous phase.

The membrane plating layer is formed, for this purpose the vacuum deposition of the noble metal and photolithography are carried out with forming the plating pattern, the noble metal layer is stripped by the reactive ion etching, thereafter the mask layer is plasma-chemically removed from the photoresist.

The membrane and the elements ("gates") of electronic means of the tunnel effect nanodetector are formed, this requires to deposit a layer of polycrystalline silicon from the gaseous phase and to carry out the photolithography for forming the pattern of the membrane and of holes on its surface as well as patterns of components of electronic means of the tunnel effect nanodetector, the layer of polycrystalline silicon and the layer of membrane plating are exposed to reactive ion etching and the mask layer of the photoresist is stripped by the plasma-chemical way, after that the selective chemical etching of the gap-forming layer from the phosphorous borosilicate glass and the layer from the silicon oxide is performed through the holes in the membrane followed by flushing the substrate in running deionized water.

BRIEF DESCRIPTION OF THE DRAWINGS

The invention and its various aspects will become more readily apparent from the following drawings:

In FIG. 1 there are designated: a substrate 1 from single crystal silicon, a sensor 2, a pin 3 of the sensor 2, a layer 4 of the noble metal deposited on the pin 3, a membrane 5 of the sensor 2, a layer 6 of the noble metal deposited on the membrane 5, a unit 7 for control the gap between the pin 3 and membrane 5, a deflection electrode 8, a tunnel current amplifier 9, an A/D converter 10, a capacitance measuring unit 11, a tunnel current limiting unit 12, through holes 13 made across the surface of the membrane 5 and in the layer 6 of the noble metal covering it.

In FIG. 2 there are designated: a substrate 1 from single crystal silicon, a sensor pin 3 made from the single crystal silicon, a layer 4 of the noble metal deposited on the pin 3, a sensor membrane 5 made from polycrystalline silicon, a layer 6 of the noble metal deposited on the membrane 5, a deflection electrode 8, through holes 13 made across the surface of the membrane 5 and in the layer 6 of the noble metal covering it, corrugations 14 on the membrane 5, components 15 of electronic means of the tunnel effect nanodetector made from polycrystalline silicon, a gap 16.

DESCRIPTION OF THE PREFERRED EMBODIMENT

Figure 1:
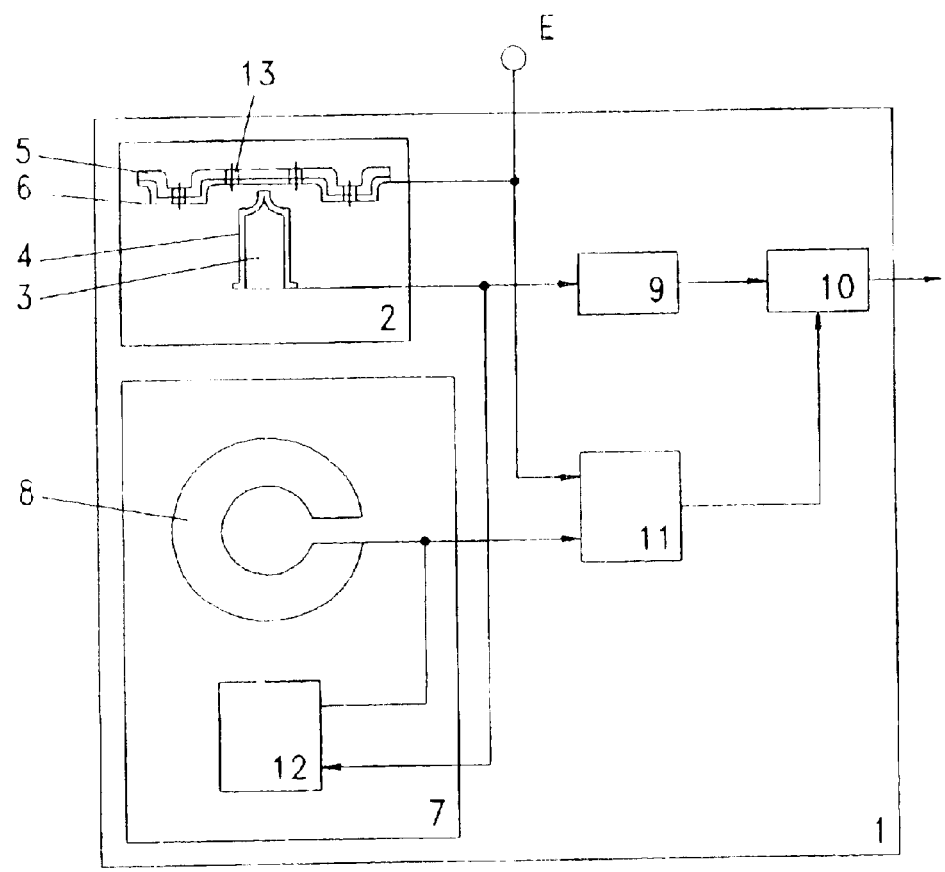
FIG. 1 is a diagrammatic view of a tunnel effect nanodetector of mechanical vibrations.
Figure 2:
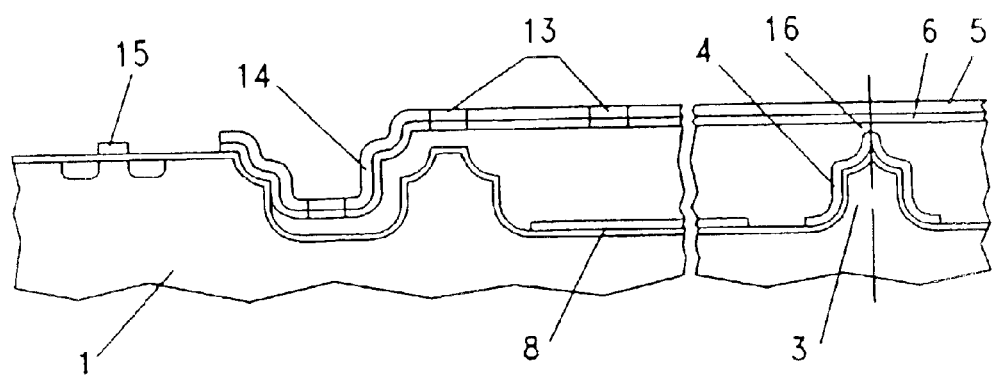
FIG. 2 is a diagrammatic view of embodiment of the tunnel effect nanodetector of mechanical vibrations explaining the method of its preparation, thereby the dimensions of the latter are shown very relative only for visual demonstration.

The tunnel effect nanodetector of mechanical vibrations (FIG. 1 and 2) is made in the form of a monolithic integrated circuit. The pin 3 of the sensitive element 2 is prepared from the single crystal silicon within the body of the substrate 1 and covered with the layer 4 of a noble metal, for example, gold. The membrane 5 of the sensitive element 2 is prepared from the polycrystalline silicon, covered with the layer 6 of a noble metal, for example gold, and placed over the pin 3 of the sensitive element 2. The through holes 13 are made across the whole surface of the membrane 5 and within the gold layer 6, the corrugations 14 are prepared along the membrane 5 boundaries. Between the pin 3 covered with the gold layer 4 and membrane 5 covered with the gold layer 6 there is available a gap 16, the size of which can vary from parts of nanometer to parts of micron.

The deflection electrode 8 made from a noble metal, for example gold, is placed around the pin 3.

The gold layer 6 deposited on the membrane 5 is coupled with a source of the input voltage and the gold layer 4 deposited on the pin 3 is coupled with the input of the tunnel current amplifier 9 and with the input of the tunnel current limiting unit 12 incorporated into the gap control unit 7 used for control the gap 16 between the pin 3 and membrane 5. The output of the tunnel current limiting unit 12 is connected to the deflection electrode 8 incorporated into the gap control unit 7.

The inputs of the capacitance measuring unit 11 are connected to the deflection electrode 8 and to the gold layer 6 deposited on the membrane 5. The outputs of the tunnel current amplifier 9 and of the capacitance measuring unit 11 are correspondingly coupled with the first and the second inputs of the A/D converter 10, the output of which is an output of the tunnel effect nanodetector of mechanical vibrations.

The tunnel effect nanodetector of mechanical vibrations operates as follows.

In the initial state, after powering, the voltage level at the deflection electrode 8 of the unit 7 for maintaining the gap 16 between the pin 3 and membrane 5 is equal to zero, in the result the gap 16 between the plating layers 4 and 6 of the sensor's 2 pin 3 and membrane 5 is large sufficiently in order to enable the tunnel current to flow through that gap. In the absence of tunnel current the capacitance measuring unit 11 measures the current capacitance value between the plating layer 6 of the membrane 5 and deflection electrode 8, having been modulated due to the action of mechanical vibrations on the membrane 5. A signal from the unit 11 enters the second input of the A/D converter 10, a digital code from that converter's output enters an external device for processing and recording.

The unit 7 for maintaining the gap between the pin 3 and membrane 5 starts to deliver a smoothly growing potential to the deflection electrode 8 and this results in appearing the Coulomb attraction force, which brings the membrane 5 nearer to the pin 3. In the case if the gap 16 is small enough, the tunnel current arises and starts to rise. When the tunnel current achieves a certain previously set value, the voltage at the deflection electrode 8 stops to rise, the mean value of the tunnel current becomes to be stable and the path for measuring the tunnel current of the nanodetector is ready to operate.

Under influence of external mechanical vibrations the membrane 5 changes its position relative to the pin 3, this has the effect of modulating the value of tunnel current. The current value of the tunnel current being amplified by the amplifier 9 enters the first input of the A/D converter 10, the digital code from the output of that converter enters an external arrangement.

With the availability of the tunnel current the path for measuring that tunnel current is more informative, than the path for measuring the capacitance value.

Given that the amplitude of external mechanical vibrations is large, the tunnel current rises steeply. As soon as the value of tunnel current is over a certain previously set value, the current limiter 12 removes the control voltage from the deflection electrode 8, this results in the sharp increase of the gap 16 and the tunnel current disappears.

For preparation of the tunnel effect nanodetector of mechanical vibrations the following operations should be successively performed.

Within the monolith of silicon substrate 1 there are formed the a pin 3 and recesses for corrugations 14 of the membrane 5 of the sensor 2, for this aim the mask layer of the silicon nitride ($Si_3N_4$) of 200 nm thickness is deposited on the substrate 1 from the gaseous phase. On the layer of silicon nitride the photolithography followed by dry etching is carried out with forming the patterns of the pin 3 and recesses for membrane 5 corrugations 14, the reactive ion etching is also carried out with the purpose to remove certain sections of silicon nitride mask layer.

The isotropic plasma-chemical etching of the mono silicon substrate 1 at a depth of $h_{etc}$=200 nm, the anisotropic reactive ion etching at a depth of $h_{etc.}$=500 nm and the local thermal (for example pyrogenic) oxidization are performed. This allows to make pin 3 of a given shape and size. After that the silicon nitride mask is stripped by the ortho-phosphoric acid ($H_3PO_4$) at the temperature of about 160° C., as well as the layer of silicon oxide is stripped by the solution of hydro-fluoric acid (HF).

The insulation layer and the plating layers for the pin 3 and deflection electrode 8 are formed, for this aim the silicon substrate is thermally oxidized at the temperature of 950° C., the silicon nitride layer is deposited from the gaseous phase and the vacuum deposition of the noble metal is performed.

Due to the fact that the most efficient tunneling of electrons between layers 4 and 6 deposited correspondingly on the pin 3 and the membrane 5 can be achieved, provided that said layers 4 and 6 are made from the gold (Au), it is necessary to do the three-layer plating: at first a titanium (Ti) layer is deposited on silicon surface for adhesion improvement, then successively the layers of platinum (Pt) and gold are deposited, therewith the platinum prevents the diffusion of silicon and titanium into gold.

On the plated gold layer the photolithography followed by dry etching is carried out with forming the plating patterns for the pin 3 and deflection electrode 8, the reactive ion etching of layers of the deposited metals is carried out, after that the mask is removed from the photoresist by plasma-chemical way.

The gap-forming layer is produced, for this aim a layer of the fusible phosphorous borosilicate glass is deposited from gaseous phase and fire-polished at the temperature of 850° C., the photolithography is carried out with obtaining the pattern of the gap-forming layer, the layer of the fusible phosphorous borosilicate glass is exposed to the reactive ion etching, after that the high-melting layer of the silicon oxide ($SiO_2$) of 200 nm thickness is deposited from the gaseous phase.

The plating layer for membrane 5 is formed, for this purpose the vacuum deposition of titanium, platinum and gold is successively performed and then the photolithography is carried out with forming the plating pattern. The plating layers (Ti—Pt—Au) are exposed to the reactive ion etching, thereafter the photoresist mask layer is plasma-chemically removed.

The membrane 5 and the elements (gates) 15 of electronic means incorporated into the tunnel effect nanodetector of mechanical vibrations are formed, this requires to deposit a layer of the polycrystalline silicon of 0.5–1 $\mu$m thickness from the gaseous phase and to carry out the photolithography for forming the pattern of the membrane 5 and holes 13 on it as well as the patterns of elements 15 of the electronic means of said tunnel nanodetector.

The layer of polycrystalline silicon and the plating layers (Ti—Pt—Au) for membrane 5 are exposed to reactive ion etching, after that with the aim to clear the membrane 5 one performs a selective chemical etching of the gap-forming layer from ortho-phosphorous borosilicate glass and the layer of silicon oxide through the holes 13 in the membrane 5 followed by flushing the substrate in running deionized water with control of the water resistivity.

Practical applicability

The tunnel effect nanodetector of mechanical vibrations is distinguished with a super high sensitivity from $10^5$ to $10^8$ B/g, wide frequency band-width from infra low frequencies close to 0 up to 150 kHz, can operate in wide temperature range from −60° C. to +60° C., all this promises a very wide field of applications.

The tunnel effect nanodetector of mechanical vibrations can be used in different diagnostics systems, for example to forecast the earthquakes, volcano eruptions, to control the ecological state of the environment, to detect the acoustical vibrations in mechanical constructions, to develop the microphones with sensitivity by 2–3 order higher than that by existing ones and enlarged distance of acoustical signal detection, to enable the development of devices for ultra-sound medical diagnostics with the by an order of magnitude greater resolution and with the radiation level reduced to the safe values.

The proposed method in conformity with the invention firstly allows to develop a tunnel effect nanodetector of mechanical vibrations in the form of a monolithic integrated circuit and to provide a high accuracy and reproducibility of constructive-functional parameters of said nanodetector and to assure high economic production factors.

The effective performance characteristics and wide application sphere for the tunnel effect nanodetector of mechanical vibrations can serve as a pledge for the practical application of the invention.

We claim:

1. A tunnel effect nanodetector, comprising:
   a sensor;
   a corrugated membrane arranged over the sensor such that a gap exists between the membrane and the sensor;
   a gap control unit operative to control a size of the gap;
   a tunnel current amplifier operatively connected to the sensor and the gap control unit;
   an A/D converter operatively connected to the tunnel current amplifier; and
   a capacitance measuring unit operative to measure capacitance between the gap control unit and the sensor,
   wherein the sensor, the membrane, the gap control unit, the tunnel current amplifier, the A/D converter, and the capacitance measuring unit comprise a monolithic integrated circuit.

2. The tunnel effect nanodetector according to claim 1, wherein the sensor comprises a probe including a pin plated with a first layer of a noble metal.

3. The tunnel effect nanodetector according to claim 2, wherein the first layer of noble metal is operatively connected to an input of the tunnel current amplifier.

4. The tunnel effect nanodetector according to claim 2, wherein the first layer of noble metal comprises gold.

5. The tunnel effect nanodetector according to claim 1, wherein the gap is variable from parts of a nanometer to parts of a micron.

6. The tunnel effect nanodetector according to claim 1, wherein a second layer of a noble metal is arranged on the membrane.

7. The tunnel effect nanodetector according to claim 6, wherein the second layer of noble metal is operatively connected to a source of input voltage.

8. The tunnel effect nanodetector according to claim 1, wherein the second layer of noble metal comprises gold.

9. The tunnel effect nanodetector according to claim 1, wherein the gap control unit comprises a deflection electrode of a noble metal arranged around a tip of the sensor.

10. The tunnel effect nanodetector according to claim 9, wherein the gap control unit comprises a unit for limiting a tunnel current value.

11. The tunnel effect nanodetector according to claim 10, wherein inputs of the capacitance measuring unit are connect to the deflection electrode, the membrane and the A/D converter.

12. The tunnel effect nanodetector according to claim 1, wherein the sensor comprises a pin.

13. The tunnel effect nanodetector according to claim 1, wherein the tunnel current amplifier is operatively connected to a first input of the A/D converter.

14. The tunnel effect nanodetector according to claim 1, wherein nanodetector has a sensitivity of $10^5$ to $10^8$ B/g and a frequency band width of 0 to 150 kHz.

15. The tunnel effect nanodetector according to claim 1, wherein an output of the tunnel current amplifier is operatively connected to the gap control unit.

16. The tunnel effect nanodetector according to claim 1, wherein boundaries of the membrane are corrugated.

17. The tunnel effect nanodetector according to claim 1, wherein the nanodetector is operative to detect mechanical vibrations.

18. The tunnel effect nanodetector according to claim 1, further comprising:
   a substrate, wherein the sensor, the membrane, the gap control unit, the tunnel current amplifier, the A/D converter, and the capacitance measuring unit are arranged on the substrate.

19. The tunnel effect nanodetector according to claim 1, wherein the membrane, the gap control unit, the tunnel current amplifier, the A/D converter, and the capacitance measuring unit comprise polycrystalline silicon.

20. The tunnel effect nanodetector according to claim 1, wherein the sensor comprises monocrystalline silicon.

21. The tunnel effect nanodetector according to claim 1, wherein the membrane comprises a plurality of through holes.

* * * * *